United States Patent
Liu et al.

(10) Patent No.: US 8,837,681 B2
(45) Date of Patent: Sep. 16, 2014

(54) METHOD AND DEVICE FOR ADJUSTING A COLLIMATOR RADIATION FIELD IN AN X-RAY IMAGING SYSTEM

(75) Inventors: Bingquan Liu, Shenzhen (CN); Yanpeng Liu, Shenzhen (CN); Juntao Song, Shenzhen (CN)

(73) Assignee: Shenzhen Mindray Bio-Medical Electronics Co., Ltd, Shenzhen (CN)

( * ) Notice: Subject to any disclaimer, the term of this patent is extended or adjusted under 35 U.S.C. 154(b) by 323 days.

(21) Appl. No.: 13/324,894

(22) Filed: Dec. 13, 2011

(65) Prior Publication Data
US 2012/0155615 A1    Jun. 21, 2012

(30) Foreign Application Priority Data

Dec. 15, 2010    (CN) .......................... 2010 1 0589757

(51) Int. Cl.
*G21K 1/04* (2006.01)
*A61B 6/06* (2006.01)

(52) U.S. Cl.
CPC ...................................... *A61B 6/06* (2013.01)
USPC ........................................................ 378/150

(58) Field of Classification Search
CPC .................................. A61B 6/06; G21K 1/02
USPC .................................. 378/150, 151, 152, 205
See application file for complete search history.

(56) References Cited

U.S. PATENT DOCUMENTS

| | | | | |
|---|---|---|---|---|
| 4,450,578 A | * | 5/1984 | Hill .............................. | 378/152 |
| 4,766,603 A | * | 8/1988 | Okabe et al. .................. | 378/152 |
| 2002/0126799 A1 | * | 9/2002 | Saladin et al. ................ | 378/152 |

* cited by examiner

*Primary Examiner* — Glen Kao
(74) *Attorney, Agent, or Firm* — Kory D. Christensen; Stoel Rives LLP (57) ABSTRACT

A method and device for adjusting a collimator radiation field and an X-ray imaging system including the device are disclosed.

22 Claims, 4 Drawing Sheets

S1 — aligning the center of the collimator to the detector

S2 — acquiring the relative distance parameter of the collimator and receiving the radiation field parameters entered by user S3 — calculating the moving parameters of each blade according to the acquired radiation field parameters and the relative distance parameter S4 — independently moving each blade according to the moving parameters to obtain the radiation field with desired size and location

METHOD AND DEVICE FOR ADJUSTING A COLLIMATOR RADIATION FIELD IN AN X-RAY IMAGING SYSTEM

CROSS-REFERENCE TO RELATED APPLICATION(S)

This application claims the benefit of Chinese Patent Application No. 201010589757.0, filed on Dec. 15, 2010, which is incorporated herein by reference in its entirety.

TECHNICAL FIELD

The following disclosure relates generally to X-ray imaging systems and, more particularly, to a method and a device for adjusting a collimator radiation field in an X-ray imaging system.

SUMMARY OF THE INVENTION

A method for adjusting a collimator radiation field in an X-ray imaging system may include aligning the center of a collimator with a detector; acquiring at least one relative distance parameter of the collimator; acquiring at least one radiation field parameter; calculating at least one moving parameters of each blade of the collimator according to the at least one radiation field parameter and relative distance parameter; and independently moving each blade according to the at least one moving parameter to obtain a radiation field with a desired size and location.

DETAILED DESCRIPTION

Usually, a collimator in an X-ray imaging system is used to adjust the X-ray radiation field. X-rays from an X-ray source tube are constrained by the collimator, such that one portion of the X-rays is blocked, while another portion projects on a specific area on the human body (hereafter referred to as the "imaging target") or on an X-ray detector.

Figure 1:
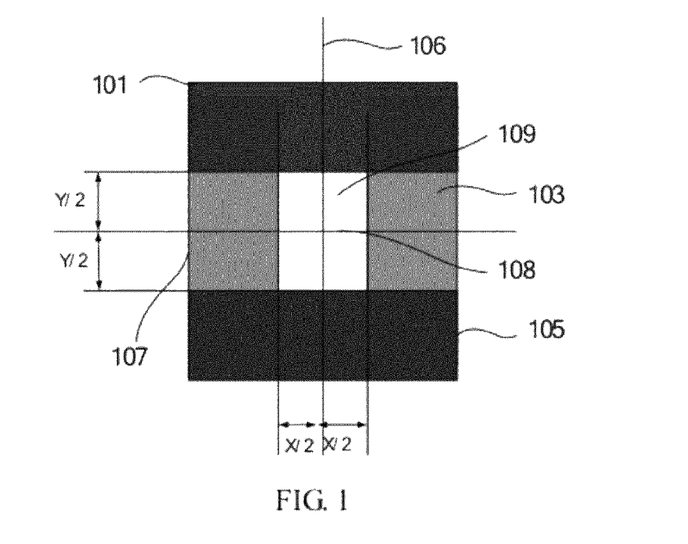
FIG. 1 is a schematic diagram of a conventional method for adjusting a radiation field.

As shown in FIG. 1, most collimators include four blades 101, 103, 105, and 107 that form a rectangular hollow 109. The rectangular hollow 109 allows X-rays to pass through. Thus, the radiation field has a symmetrical shape corresponding to the rectangular hollow. In other words, the left and right boundaries of the radiation field are symmetrical to the center line 106 of the X-ray beam, and the upper and lower boundaries are symmetrical to the center line 108 of the X-ray beam.

When the user wants the radiation field to be smaller, he or she presses a control button or the like, after which each pair of parallel blades in the collimator symmetrically moves closer by the same distance to make the hollow narrower. A narrower hollow leads to a smaller radiation field. For example, if the hollow rectangle has a width of X and a length of Y, the blade 101 and blade 105 (or blades 103 and 107) are controlled to move toward the center line 108 (or 106) for Y/2 (or X/2) to close the collimator, reducing the radiation field. Similarly, a larger hollow results in a larger radiation field.

In some X-ray imaging systems, such as a U-arm X-ray imaging system, the collimator is fixed on the X-ray source tube, which is fixed on one end of a U-arm supporter. The detector (or receptor) is fixed on the other end of the U-arm supporter. The U-arm supporter cannot be moved after being installed in an imaging room. Therefore, the collimator keeps still in such a manner that the center of the collimator aligns to the center of the detector.

In addition, as mentioned above, the blades in each pair moves symmetrically toward each other during adjustment of the radiation field. As a result, the center of the radiation field remains at the center of the detector during adjustment of the radiation field. This sometimes necessitates movement of the examination table for supporting the imaging target to ensure that the center of the region of interest (ROI) of the imaging target is located at the center of the radiation field. However, frequent movement of the examination table may be uncomfortable to the patient.

In some X-ray systems, such as a ceiling-mounted X-ray imaging system, the whole X-ray tube can be moved independently. Thus, the center of the radiation field can change freely along with the movement of the X-ray tube. However, this kind of X-ray system often has low adjustment accuracy due to the bulky mechanical structure of the ceiling mount. Thus, it is difficult to control the location of the radiation field.

The following disclosure provides for freely adjusting the radiation field of the X-ray imaging system by independently regulating the blades of the collimator, thus obtaining the most accurate location of the radiation field. As a result, better quality images can be obtained.

In one embodiment of an X-ray imaging system according to the present disclosure, the imaging system may include an X-ray source tube, a detector, a collimator, a motor, and a control device. The X-ray tube is used for emitting X-rays, and can be fixed on one end of a supporter, such as, for example, a U-arm supporter, a C-arm supporter, or a ceiling-mounted telescope supporter, and the like. The detector is used for receiving the X-rays and transforming the X-rays into readable signals, such as electrical signals. The detector may be located facing the X-ray source tube. For example, the detector can be fixed on the other end of the U-arm supporter or C-arm supporter, or on a column standing on the ground opposite the telescope.

The collimator includes at least three blades, which can form a hollowed polygon. The collimator may be fixed on the X-ray source tube. By independently driving each blade of the collimator, the center and/or area of the hollowed polygon can be changed. As a result, many kinds of radiation fields with different locations and/or sizes can be achieved without moving the X-ray source tube or the examination table. The motor can be controlled by the control device for independently driving the motion of the blades. The control device may be used for control of the entire X-ray imaging system. In some embodiments, a collimator control device may be included in the control device, and the collimator control device may be used for at least controlling the motor for driving the blades.

Figure 2:
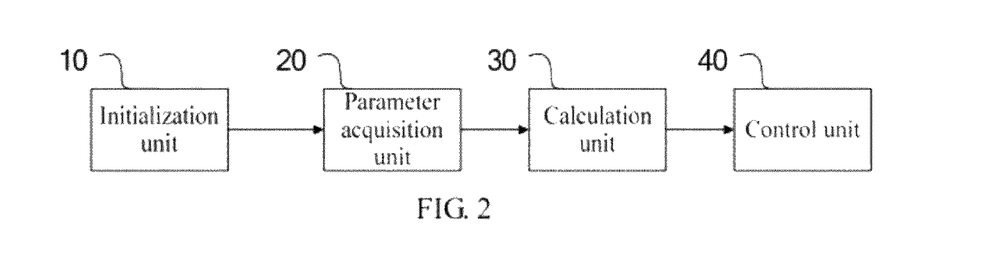
FIG. 2 is a block diagram of a collimator radiation field adjusting device.

Referring to FIG. 2, one embodiment of a collimator control device includes an initialization unit 10, a parameter acquisition unit 20, a calculation unit 30, and a control unit 40. The initialization unit 10 may be used for initializing the collimator, for example, by aligning the center of the collimator with the detector; that is, making the line crossing the center of the collimator and the center of the detector be perpendicular with the surface of the detector. The parameter acquisition unit 20 may acquire parameters for controlling the movement of the blades, such as, for example, the distance between the X-ray source and the blades, the blade moving parameters input by the user, and the like. The calculation unit 30 may calculate the moving distance of each blade according to the acquired parameters. The control unit 40 may control the movement of the blades according to the calculated moving distance of each blade.

Figure 6:
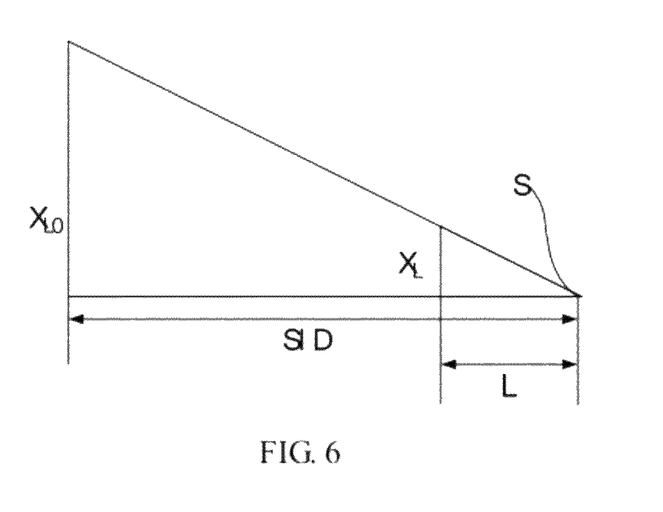
FIG. 6 is a schematic diagram of a moving parameter calculating step in a radiation field adjusting method.

The collimator control device may be regarded as a device for adjusting the collimator radiation field. The collimator control device may be a component of an X-ray imaging system. A skilled artisan will recognize that an X-ray imaging system may include an X-ray source for producing X-rays, a detector for receiving X-ray signals and transforming the X-ray signals to image signals, and a collimator for constraining the X-rays to obtain a radiation field projected on an imaging target which may lie on or stand before the detector. The collimator may be located between the X-ray source and the detector. Referring to FIG. 6, the S may be regarded as an X-ray source, the shorter vertical line $X_L$ may be regarded as the collimator (or blades), and the longer vertical line $X_{L0}$ may be regarded as the detector.

In some embodiments, the collimator control device may be embodied as a single integrated circuit (IC) chip, or, in other embodiments, it can be embodied as a printed circuit board (PCB) or as a general purpose or special purpose processor executing instructions stored in a memory.

Figure 3:
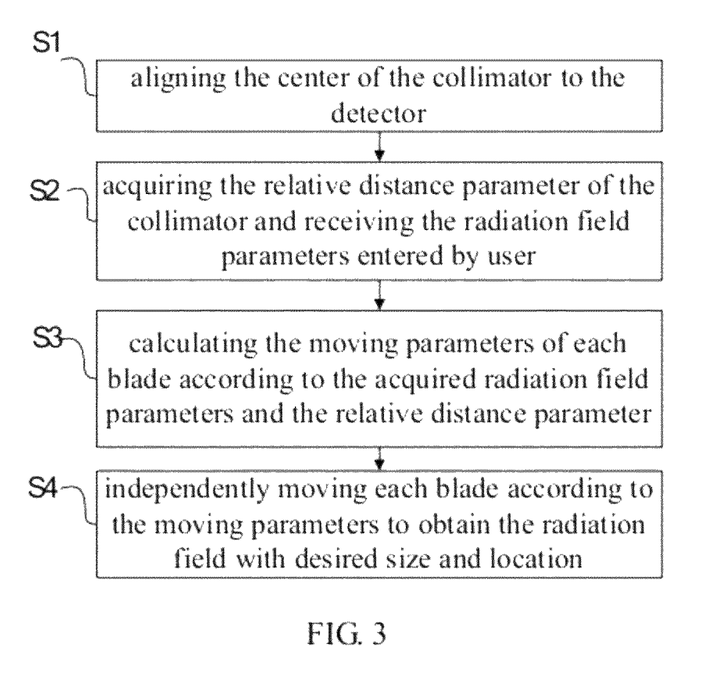
FIG. 3 is a flow chart of a collimator radiation field adjusting method.

Referring to FIG. 3, one embodiment of a radiation field adjusting method may include the following steps.

Step 1 (S1): aligning the center of the collimator with the detector.

In one embodiment, all of the blades are reset to an initial position. The initial position can be set as the position where the blades form a very small rectangular hollow that allows the X-rays passing through to only irradiate the center point of the detector; that is, a position nearly blocking all the X-rays. The center of the rectangular hollow may be regarded as the center of the collimator.

Step 2 (S2): acquiring one or more relative distance parameters of the collimator and receiving one or more radiation field parameters entered by the user;

Based on the imaging target and the imaging type or other related conditions, the user can decide a region of the target to be irradiated. In one embodiment, the user may choose or enter the size and location of the radiation field through an interactive interface, such as a control board, a touch screen, etc. Meanwhile, one or more relative distance parameters, such as the distance from the blade to the X-ray source and/or the SID (Source Image Distance), may be read from storage or detected by the system. For example, the distance from the blade to the X-ray source may be a constant stored in the system or a changeable and measurable parameter controlled by the system. In this disclosure, the SID refers to the distance from the X-ray source to the image plane or the distance from the X-ray source to the detector surface, since the detector plane can be regarded as the image plane in most cases. The SID can be a changeable and measurable parameter controlled by the system or a radiation field parameter entered by the user. In various embodiments, step 2 can be performed before step 1.

Step 3 (S3): calculating one or more moving parameters of each blade according to the one or more radiation field parameters and relative distance parameters.

After the one or more relative distance parameters and radiation field parameters are determined, the system may calculate moving parameters for each blade. The moving parameters may include, for example, the moving direction and the moving distance for each blade.

Step 4 (S4): independently moving each blade according to the one or more moving parameters to obtain a radiation field with the desired size and location.

In one embodiment, the user may enter the radiation field parameters to the imaging system, and the radiation field adjustment device may calculate the blade moving parameters according to the radiation field parameters and the distance parameters. Thus, the motor can receive driving instructions based on the moving parameters for each blade from the radiation field adjustment device. In one embodiment, the motor can drive each blade independently. As a result, either the size or the location of the radiation field may be adjusted as desired.

Figure 4:
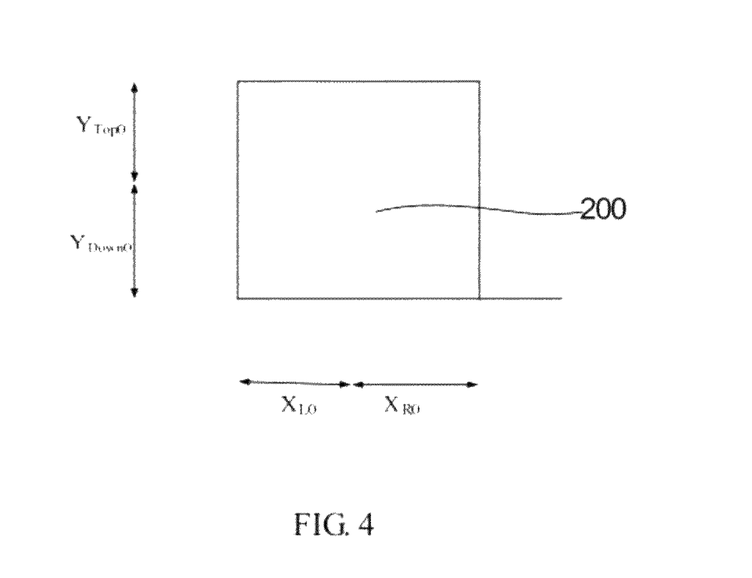
FIG. 4 is a schematic diagram of a radiation field obtained by a collimator radiation field adjusting method.
Figure 5:
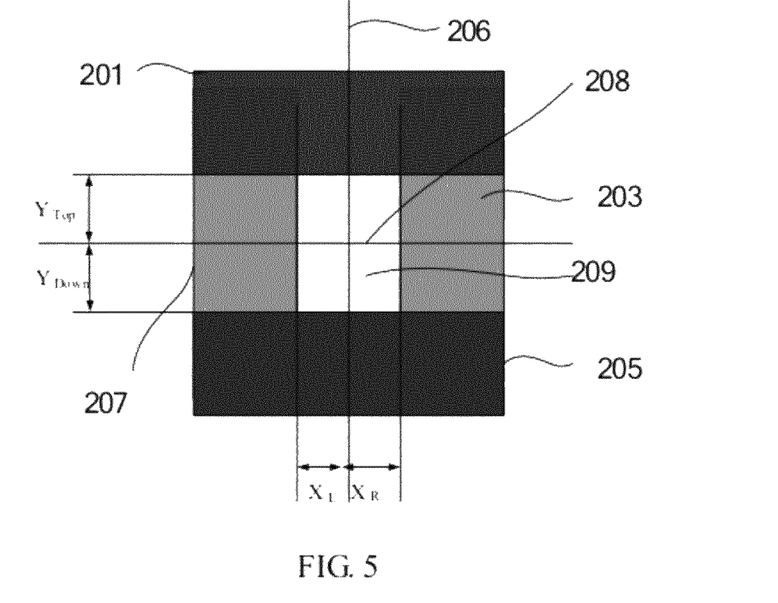
FIG. 5 is a schematic diagram of a collimator containing four blades in an X-ray imaging system.

Referring to FIGS. 4 and 5, the X-ray radiation field 200 projected on an imaging target (or the detector) has a rectangular shape in one embodiment, as the collimator may include four blades 201, 203, 205 and 207, forming a rectangular hollow 209. However, the collimator can also include three blades, which can form a triangular hollow and a triangular radiation field. The collimator may also have five or more blades. Different shapes of the radiation field can be obtained according to the different number of blades or configurations of the collimator.

The radiation field adjusting method may include various other steps, as described below.

In one embodiment, the method may include aligning the center of the collimator to the detector. Thereafter, the method may include receiving or acquiring the radiation field parameters.

In one embodiment, users can manually enter some parameters to determine the shape and size of the radiation field. Such parameters may include, for example, the length/width value of the radiation field, and/or the SID value. For example, as shown in FIG. 4, the user may enter the distance from the center of the radiation field 200 to each boundary line. The distance can be labeled as $X_{L0}$, $X_{R0}$, $Y_{Top0}$, and $Y_{Down0}$.

The $X_{L0}$ value represents the distance from the center of the radiation field to the left boundary. The $X_{R0}$ value represents the distance from the center of the radiation field to the right boundary. The $Y_{Top0}$ value represents the distance from the center of the radiation field to the top boundary. The $Y_{Down0}$ value represents the distance from the center of the radiation field to the bottom boundary. However, these parameters may also be determined by the system automatically. For example, an imaging system may have intelligent patient identification and/or radiation field determination.

The SID may also be acquired manually or automatically. For example, the SID can be sensed by the parameter acquisition unit 20 or can be read from a memory or a LUT (look-up table), which stores different SID values for different imaging applications and/or performance.

The method may also include acquiring the relative distance parameter(s) of the collimator.

In FIG. 6, the relative distance parameter of the collimator may be the distance from the blades to the X-ray source. The point S in FIG. 6 may represent the location of the X-ray source, and the distance L may represent the distance from the blades to the X-ray source. The relative distance parameter may be acquired in order to calculate the blade moving parameters. Therefore, the distance L may be replaced by other relative distance parameters, which may be used for calculating the blade moving parameters. The SID may also be regarded as a relative distance parameter.

The method may also include calculating the moving parameters of each blade according to the acquired radiation field parameters and relative distance parameters.

When the radiation field parameters $X_{L0}$, $X_{R0}$, $Y_{Top0}$, and $Y_{Down0}$ and the relative distance parameters L and SID are determined, the calculation unit 30 may calculate the blade moving parameters, such as the moving distance and direction of each blade. One example of the calculation is shown in the following equations:

$$X_L = (L * X_{L0})/\text{SID}; \tag{1}$$

$$X_R = (L * X_{R0})/\text{SID}; \tag{2}$$

$$Y_{Top} = (L * Y_{Top0})/\text{SID}; \text{ and} \tag{3}$$

$$Y_{Down} = (L * Y_{Down0})/\text{SID}. \tag{4}$$

The $X_L$ value represents the moving distance of the left blade 207. The $X_R$ value represents the moving distance of the right blade 203. The $Y_{Top}$ value represents the moving distance of the top blade 201. The $Y_{Down}$ value represents the moving distance of the bottom blade 205. In one embodiment, the moving direction can be determined by comparing the initial distance of the blade to the collimator center with the blade moving distance. Alternatively, it may be preset by the system.

The method may further include independently moving each blade according to the moving parameters to obtain a radiation field with a desired size and location.

After the blade moving parameters are determined, the corresponding radiation field has also been determined. Executing the blade moving step can realize the adjustment of the radiation field. In some embodiments, the system can employ one motor to drive each blade in turn, or employ four motors to drive each blade respectively. It can also employ two motors, which each motor responsible for driving a pair of blades, such as the parallel blades 201 and 205, or the blades 203 and 207. When a greater number of motors is employed, the \desired radiation field can be achieved more quickly.

Figure 7:
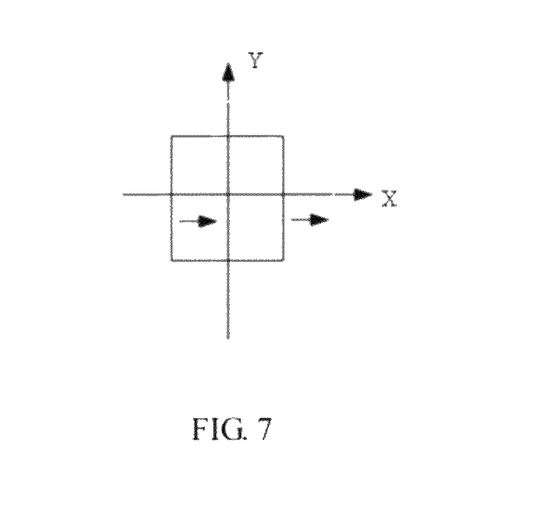
FIG. 7 is a schematic diagram of moving directions of the blades of the collimator in a radiation field adjusting method.

Referring to FIG. 7, the opposing blades 207 and 203 can be driven along the X axis in the same direction. Thus the center of the radiation field can be changed without moving the X-ray source tube. When the moving distances of the blades are different, whether the moving directions are the same or in opposite directions, the center may change without moving the X-ray source tube. Similarly, the opposing blades 201 and 205 may be driven along the Y axis in the same direction or in opposite directions.

Figure 8:
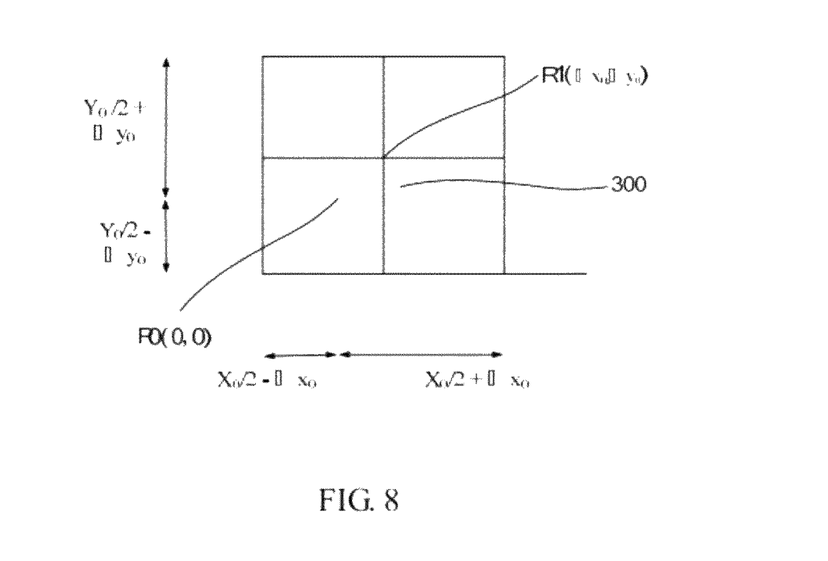
FIG. 8 is a schematic diagram of a radiation field obtained by a collimator radiation field adjusting method.

Referring to FIG. 8, a radiation field adjusting method may include the following steps.

The method may include aligning the center of the collimator to the detector.

The initial center R0 of the radiation field (or the detector) may be assumed to have the coordinate of (0, 0). If each pair of opposing blades moves toward or away from the center of the collimator by the same distance, the center of the radiation field will stay at R0.

The method may also include receiving/acquiring the radiation field parameters.

In one embodiment, the radiation field parameters may include the width and length of the desired radiation field and an offset of the radiation field center. For example, the user may manually enter or choose the width $Y_0$ and the length $X_0$ of the radiation field and the offset of the radiation field center identified as a relative coordinate ($\Delta x_0$, $\Delta y_0$). The relative coordinate $\Delta x_0$, $\Delta y_0$) may represent the location of the center of the desired radiation field relative to the location of the initial center of the radiation field (or the center of the detector). In one embodiment, the SID may be regarded as one of the parameters of the radiation field and acquired in step 22.

The method may further include acquiring the relative distance parameter(s) of the collimator.

Relative distance parameter(s), such as the distance from the blades to the X-ray source, may be acquired for calculating the blade moving parameters. The distance L may be used to represent the distance from the blades to the X-ray source. Similarly, the distance L can be replaced by other relative distance parameter(s), which can be used for calculating the blade moving parameters. The SID can be regarded as a relative distance parameter, which is acquired manually or automatically in this step.

The method may also include calculating the moving parameters of each blade according to the acquired radiation field parameters and the relative distance parameters.

When the radiation field and the relative distance parameters are determined, the moving parameter(s) of each blade can be calculated by the system or the calculation unit 30. In this embodiment, the calculation may proceed using the equations listed below:

$$X_L = (L * (X_0/2 - \Delta x_0))/\text{SID}; \tag{1}$$

$$X_R = (L * (X_0/2 + \Delta x_0))/\text{SID}; \tag{2}$$

$$Y_{Top} = (L * (Y_0/2 + \Delta y_0))/\text{SID}; \text{ and} \tag{3}$$

$$Y_{Down} = (L * (Y_0/2 - \Delta y_0))/\text{SID}. \tag{4}$$

The $X_L$ value may represent the moving distance of the left blade 207. The $X_R$ value may represent the moving distance of the right blade 203. The $Y_{Top}$ value may represent the moving distance of the top blade 201. The $Y_{Down}$ value may represent the moving distance of the bottom blade 205. The moving direction may be determined by the value of each moving distance according to one or more system settings. For example, if $X_L$ is a negative value, the left blade 207 may move toward the right blade 203. If $X_L$ is a positive value, the left blade 207 may move away from the right blade 203. If $X_R$ is a negative value, the right blade 203 may move toward the left blade 207. If $X_R$ is a positive value, the right blade 203 may move away from the left blade 207. The top blade 201 and the bottom blade 205 may work similarly.

The method may also include independently moving each blade according to the moving parameters to obtain the radiation field with the desired size and location.

Executing the blade moving step may result in the desired radiation field. In one embodiment, the system may employ one motor to drive each blade in turn or employ four motors to respectively drive each blade. The system may also employ two motors, each motor being responsible for driving a pair of blades, such as the parallel blades 201 and 205, or the blades 203 and 207.

According to the foregoing embodiments, the center/location of the radiation field can be easily changed due to the independent movement of each blade. When the radiation field adjusting method or the device of this disclosure is applied to a U-arm or C-arm X-ray imaging system, the location and size of the radiation field can be adjusted without moving the X-ray source tube or the detector/examination table, thus making the patient feel more comfortable. In another situation, if the radiation field adjusting method or device is applied to a ceiling mounted X-ray imaging system, the independent moving of each blade can make fine adjustments to the radiation field when misalignment of the collimator to the detector occurs. As a result, more accurate positioning of the radiation field can be achieved.

This disclosure has been made with reference to various exemplary embodiments including the best mode. However, those skilled in the art will recognize that changes and modifications may be made to the exemplary embodiments without departing from the scope of the present disclosure. For example, various operational steps, as well as components for carrying out operational steps, may be implemented in alternative ways depending upon the particular application or in consideration of any number of cost functions associated with the operation of the system (e.g., one or more of the steps may be deleted, modified, or combined with other steps).

Additionally, as will be appreciated by one of ordinary skill in the art, principles of the present disclosure may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-ray Discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof are intended to cover a non-exclusive inclusion, such that a process, a method, an article, or an apparatus that comprises a list of elements does not include only those elements but may include other elements not expressly listed or inherent to such process, method, system, article, or apparatus. Those having skill in the art will appreciate that many changes may be made to the details of the above-described embodiments without departing from the underlying principles of the invention. The scope of the present invention should, therefore, be determined only by the following claims.

What is claimed is:

1. A method for adjusting a collimator radiation field of an X-ray imaging system, comprising:
   aligning the center of a collimator to a detector;
   acquiring at least one radiation field parameter and at least one relative distance parameter of the collimator;
   respectively calculating at least one moving parameter of each blade of the collimator according to the at least one radiation field parameter and the at least one relative distance parameter; and
   independently moving each blade according to the at least one moving parameter.

2. The method of claim 1, wherein the at least one radiation field parameter comprises the distance from the center of the radiation field to each boundary of the radiation field.

3. The method of claim 2, wherein the radiation field is a rectangular shape, and the at least one radiation field parameter comprises $X_{L0}$, $X_{R0}$, $Y_{Top0}$, and $Y_{Down0}$, wherein $X_{L0}$ represents the distance from the center of the radiation field to a left boundary, $X_{R0}$ represents the distance from the center of the radiation field to a right boundary, $Y_{Top0}$ represents the distance from the center of the radiation field to a top boundary, and $Y_{Down0}$ represents the distance from the center of the radiation field to a bottom boundary.

4. The method of claim 1, wherein the at least one relative distance parameter comprises the distance from the blades to an X-ray source.

5. The method of claim 4, wherein the at least one relative distance parameter comprises a source image distance (SID) of the X-ray imaging system.

6. The method of claim 4, wherein the at least one radiation field parameter comprises a source image distance (SID) of the X-ray imaging system.

7. The method of claim 6, wherein the at least one moving parameter of each blade is calculated according to the following equations:

$$X_L = (L * X_{L0})/\text{SID};$$

$$X_R = (L * X_{R0})/\text{SID};$$

$$Y_{Top} = (L * Y_{Top0})/\text{SID}; \text{ and}$$

$$Y_{Down} = (L * Y_{Down0})/\text{SID};$$

wherein L represents the distance from the blades to an X-ray source, $X_L$, $X_R$, $Y_{Top}$, and $Y_{Down}$ represent the at least one moving parameter of each blade, respectively, and SID represents the distance from the X-ray source to the detector; wherein $X_{L0}$ represents the distance from the center of the radiation field to a left boundary, $X_{R0}$ represents the distance from the center of the radiation field to a right boundary, $Y_{Top0}$ represents the distance from the center of the radiation field to a top boundary, and $Y_{Down0}$ represents the distance from the center of the radiation field to a bottom boundary.

8. The method of claim 1, wherein the at least one radiation field parameter comprises a source image distance (SID), width $X_0$, and length $Y_0$ of the radiation field, and an offset ($\Delta x_0$, $\Delta y_0$) of the radiation field center, the at least one relative distance parameter comprising the distance from the blades to an X-ray source.

9. The method of claim 8, wherein the at least one moving parameter of each blade is calculated according to the following equations:

$$X_L=(L*(X_0/2-\Delta x_0))/SID;$$

$$X_R=(L*(X_0/2+\Delta x_0))/SID;$$

$$Y_{Top}=(L*(Y_0/2+\Delta y_0))/SID; \text{ and}$$

$$Y_{Down}=(L*(Y_0/2-\Delta y_0))/SID;$$

wherein L represents the distance from the blades to an X-ray source; $X_L$, $X_R$, $Y_{Top}$, and $Y_{Down}$ represent the at least one moving parameter of each blade, respectively; $\Delta x_0$ and $\Delta y_0$ represent offset coordinates of the center of the radiation field relative to the center of the detector with a relative coordinate of (0, 0); and SID represents the distance from the X-ray source to the detector.

10. A device for adjusting a collimator radiation field of an X-ray imaging system, comprising:
an initialization unit for aligning the center of a collimator to a detector;
a parameter acquisition unit for acquiring at least one radiation field parameter and at least one relative distance parameter of the collimator;
a calculation unit for respectively calculating at least one moving parameter of each blade of the collimator according to the at least one radiation field parameter and relative distance parameter; and
a control unit for independently moving each blade according to the at least one moving parameter.

11. The device of claim 10, wherein the at least one radiation field parameter comprises the distance from the center of the radiation field to each boundary of the radiation field.

12. The device of claim 11, wherein the radiation field is a rectangular shape, and the at least one radiation field parameter comprises $X_{L0}$, $X_{R0}$, $Y_{Top0}$, and $Y_{Down0}$, wherein $X_{L0}$ represents the distance from the center of the radiation field to a left boundary, $X_{R0}$ represents the distance from the center of the radiation field to a right boundary, $Y_{Top0}$ represents the distance from the center of the radiation field to a top boundary, and $Y_{Down0}$ represents the distance from the center of the radiation field to a bottom boundary.

13. The device of claim 10, wherein the at least one relative distance parameter comprises the distance from the blades to an X-ray source.

14. The device of claim 13, wherein the at least one relative distance parameter further comprises the source image distance (SID) of the X-ray imaging system.

15. The device of claim 10, wherein the at least one radiation field parameter comprises a source image distance (SID) of the X-ray imaging system.

16. The device of claim 15, wherein the at least one moving parameter of each blade is calculated according to the following equations:

$$X_L=(L*X_{L0})/SID;$$

$$X_R=(L*X_{R0})/SID;$$

$$Y_{Top}=(L*Y_{Top0})/SID;$$

$$Y_{Down}=(L*Y_{Down0})/SID;$$

wherein L represents the distance from the blades to an X-ray source, $X_L$, $X_R$, $Y_{Top}$, and $Y_{Down}$ represent the at least one moving parameter of each blade respectively, and SID represents the distance from the X-ray source to the detector; wherein $X_{L0}$ represents the distance from the center of the radiation field to a left boundary, $X_{R0}$ represents the distance from the center of the radiation field to a right boundary, $Y_{Top0}$ represents the distance from the center of the radiation field to a top boundary, and $Y_{Down0}$ represents the distance from the center of the radiation field to a bottom boundary.

17. The device of claim 10, wherein the radiation field parameter comprises a source image distance (SID), width $X_0$, and length $Y_0$ of the radiation field, and an offset ($\Delta x_0$, $\Delta y_0$) of the radiation field center, the at least one relative distance parameter comprising the distance from the blades to an X-ray source.

18. The device of claim 17, wherein the at least one moving parameter of each blade is calculated according to the following equations:

$$X_L=(L*(X_0/2-\Delta x_0))/SID;$$

$$X_R=(L*(X_0/2+\Delta x_0))/SID;$$

$$Y_{Top}=(L*(Y_0/2+\Delta y_0))/SID; \text{ and}$$

$$Y_{Down}=(L*(Y_0/2-\Delta y_0))/SID;$$

wherein L represents the distance from the blades to an X-ray source; $X_L$, $X_R$, $Y_{Top}$, and $Y_{Down}$ represent the at least one moving parameter of each blade, respectively; $\Delta x_0$ and $\Delta y_0$ represent offset coordinates of the center of the radiation field relative to the center of the detector with a relative coordinate of (0, 0); and SID represents the distance from the X-ray source to the detector.

19. An X-ray imaging system, comprising:
an X-ray source for producing X-rays;
a detector for receiving X-ray signals and transforming the X-ray signals to image signals;
a collimator comprising a plurality of blades, located between the X-ray source and the detector, for constraining the X-rays to a particular radiation field; and
a device for adjusting the radiation field, comprising:
an initialization unit for aligning the center of a collimator to the detector;
a parameter acquisition unit for acquiring at least one radiation field parameter and at least one relative distance parameter of the collimator;
a calculation unit for respectively calculating at least one moving parameter of each blade of the collimator according to the at least one radiation field parameter and relative distance parameter; and
a control unit for independently moving each blade according to the at least one moving parameter.

20. The X-ray imaging system of claim 19, wherein the radiation field parameter comprises the distance from the center of the radiation field to each boundary of the radiation field.

21. The X-ray imaging system of claim 20, wherein the collimator comprises four blades forming a rectangular hollow.

22. The X-ray imaging system of claim 20, wherein the collimator comprises three blades forming a triangular hollow.

\* \* \* \* \*